United States Patent [19]

Perusek et al.

[11] Patent Number: 4,651,007
[45] Date of Patent: Mar. 17, 1987

[54] MEDICAL DIAGNOSTIC MECHANICAL POSITIONER

[75] Inventors: Allan J. Perusek, Mentor; Ernest F. Jablonski, W. Farmington, both of Ohio

[73] Assignee: Technicare Corporation, Cleveland, Ohio

[21] Appl. No.: 650,372

[22] Filed: Sep. 13, 1984

[51] Int. Cl.$^4$ .............................................. G01T 1/166
[52] U.S. Cl. ................................. 250/363 S; 378/189; 378/15; 378/17
[58] Field of Search ................... 250/363 SC, 363 SF; 378/177, 189, 195, 209, 20, 196, 197, 15, 17

[56] References Cited

U.S. PATENT DOCUMENTS

| | | | |
|---|---|---|---|
| 3,575,600 | 4/1971 | Trachevski | 378/189 |
| 3,809,886 | 5/1974 | Cochran et al. | 378/196 |
| 3,848,132 | 11/1974 | Foderaro | 378/209 |
| 4,158,777 | 6/1979 | Hogan | 378/196 |
| 4,426,578 | 1/1984 | Bradcovich et al. | 378/15 |
| 4,473,749 | 9/1984 | Derenzo et al. | 250/363 SC |

Primary Examiner—Carolyn E. Fields
Assistant Examiner—Richard Hanig
Attorney, Agent, or Firm—Audley A. Ciamporcero, Jr.; M. A. Kaufman

[57] ABSTRACT

A mechanical support structure which coordinates patient positioning and medical diagnostic equipment positioning in a unified system. More particularly, the system includes a vertically adjustable patient table supported at both ends by substantial upright end support members. Also suspended between these two end supports is a radiation detector such as a scintillation camera head whose position relative to the patient table is conveniently and accurately adjustable from an operator control panel provided on one end support. Each degree of freedom afforded the detector is accomplished independently of the other and, if desired, simultaneously, or in any desired combination. To perform static imaging the separation between the detector and the patient table is adjustable, as is the lateral position of the detector between the two end stands and hence along the span of the patient table. In a detector having a non-symmetrical field of view, its length and width orientation may be reversed. The plane of focus of the detector is selectable within a range of pivot angles. Alternatively, to accomplish ECT imaging, the detector is orbited about the patient at a selected intermediate position between the two end stands and at a selected radius of rotation. This orbital motion may be circular relative to a fixed patient position or, if desired, may be non-circular by adjusting the radial position of the scintillation detector, the height of the support structure or a synchronized combination of both. In non-circular orbital motion, the detector may also be rotated off of a radial focus.

15 Claims, 17 Drawing Figures

MEDICAL DIAGNOSTIC MECHANICAL POSITIONER

FIELD OF THE INVENTION

This invention relates to a mechanical system that integrates a movable patient support with a movable diagnostic detector particularly useful in diagnostic imaging such as nuclear medicine.

BACKGROUND OF THE INVENTION

In prior nuclear medicine or gamma ray camera systems, the scintillation camera head or radioisotope detector and the patient support, typically a table, are separate, independent apparatus. While such scintillation camera systems have existed for about two decades now, performing to a greater or lesser degree satisfactorily, the advances in resolution in newer systems have created greater requirements in precision alignment between the detector and the patient support. This has been particularly noticeable as nuclear camera systems have been used more and more for generating tomographic images by rotation of the detector about the patient, in addition to the more conventional static imaging. One such nuclear camera system capable of both whole body static imaging as well as emission computed tomography or ECT, is the Omega 500 system available from Technicare Corporation, Solon, Ohio 44139, and described in U.S. Pat. No. 4,426,578 to Bradcovich, et al.

In general, all prior nuclear camera systems known to applicants, whether or not including ECT capability, feature a cantilevered table separate from the imaging apparatus. All such systems suffer in image quality from unwanted motion between the patient support and the detection device. In an ECT-type system, unwanted motion is contributed by mechanical flexure in the cantilevered patient support, mechanical flexure from the rotating cantilevered structure supporting the scintillation detector or camera head and from a lack of precision alignment between the two, particularly during rotation of the camera head.

SUMMARY OF THE INVENTION

We have invented a stable, multipurpose mechanical diagnostic imaging support structure which obviates the need for a cantilevered patient table while allowing for static, linear and rotational imaging such as by a rotatable scintillation detector.

In a preferred embodiment, our apparatus comprises a pair of spaced apart end stands between which a removable patient table is supported in a manner that permits vertical adjustment of the table. Also supported between the end stands is at least one pair of substantial solid rods which, in turn, support a scintillation detector in a manner that allows the scintillation detector to be (a) horizontally displaced to a desired position within the two ends stands; (b) pivoted about an axis orthogonal to the aforementioned permissible horizontal displacement to permit angular displacement of the plane of the field of view; and (c) rotated about a vertical axis orthogonal to both the pivotal axis and the horizontal displacement axis to alter the length/width orientation of the field of view of the scintillation detector.

In addition to these three degrees of motion, the entire detector is vertically adjustable independent of the vertical position of the patient support by lowering or raising the pair of rods supporting the detector. These rods are retained at their respective ends by a pair of synchronized rotatable subassemblies, one in each end stand, which permits the detector head to be positioned in nonparallel fashion, at an angle relative to the plane defined by the patient table. Finally, the subassemblies themselves are positioned within a larger rotatable member that serves to rotate the rods, including the scintillation detector, in orbital fashion about a patient to perform ECT.

In all, there are seven motions, three of which relate directly to the detector, independent of any motion in the end stands, while the remaining four occur within the end stands. These latter four are accomplished preferably independently of each other and each preferably by a single power source in one end stand with the motion duplicated synchronously in the other.

DETAILED DESCRIPTION OF THE INVENTION

Figure 1:
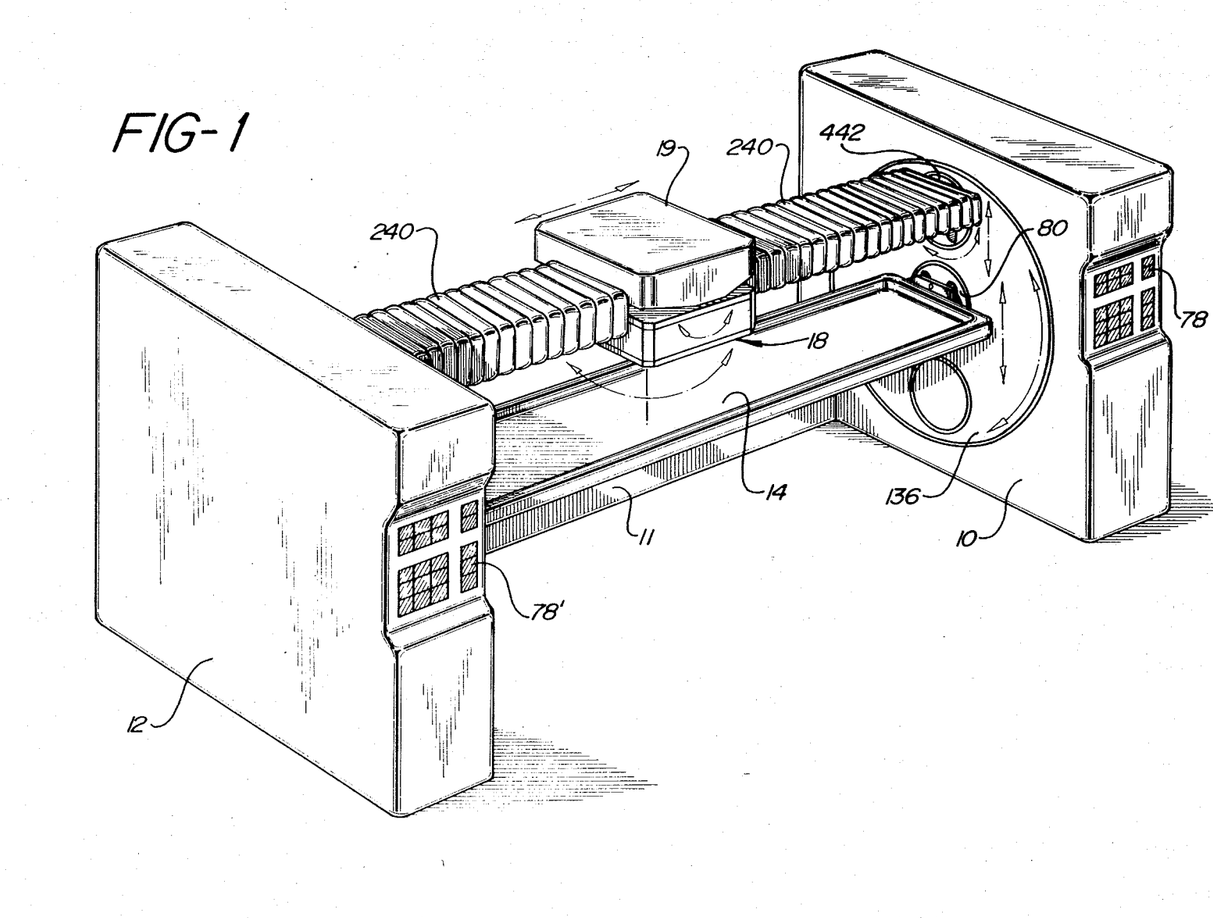
FIG. 1 is a perspective view of a medical diagnostic mechanical positioner in accordance with the present invention having one scintillation detector and a patient table of the type particularly suitable for whole body scanning.
Figure 2:
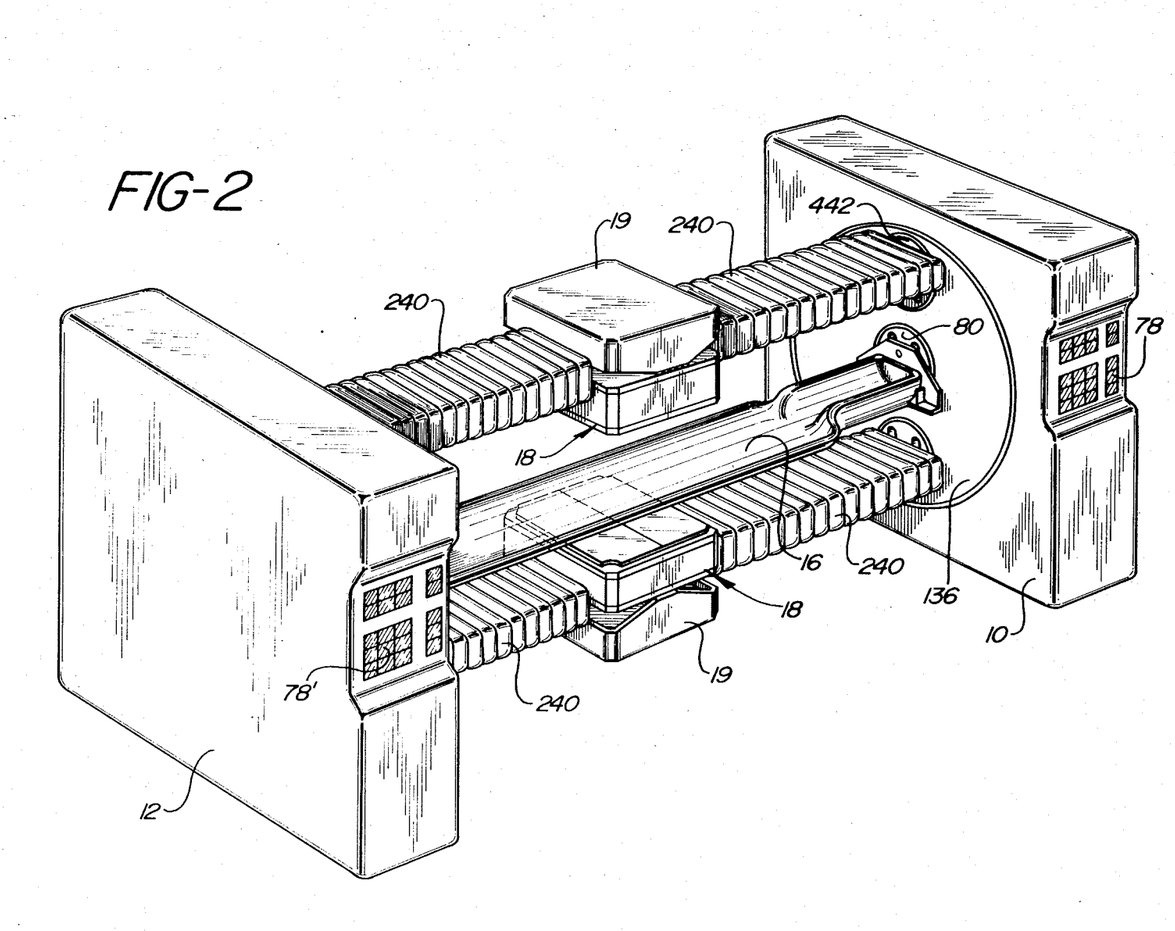
FIG. 2 is a perspective view showing an alternative embodiment of the diagnostic positioner of FIG. 1 showing a pair or diametrically opposed scintillation detectors rotatable about a patient table of the type specially designed for ECT.
Figure 3:
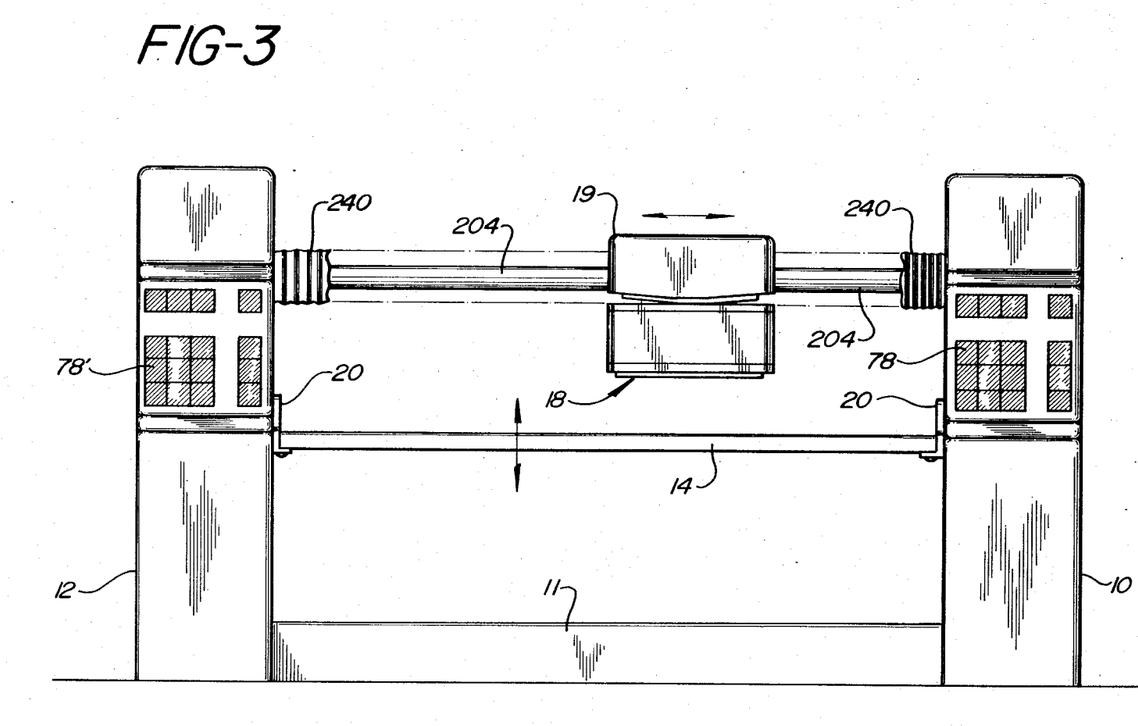
FIG. 3 is a front elevational view of the positioner of FIG. 1.
Figure 4:
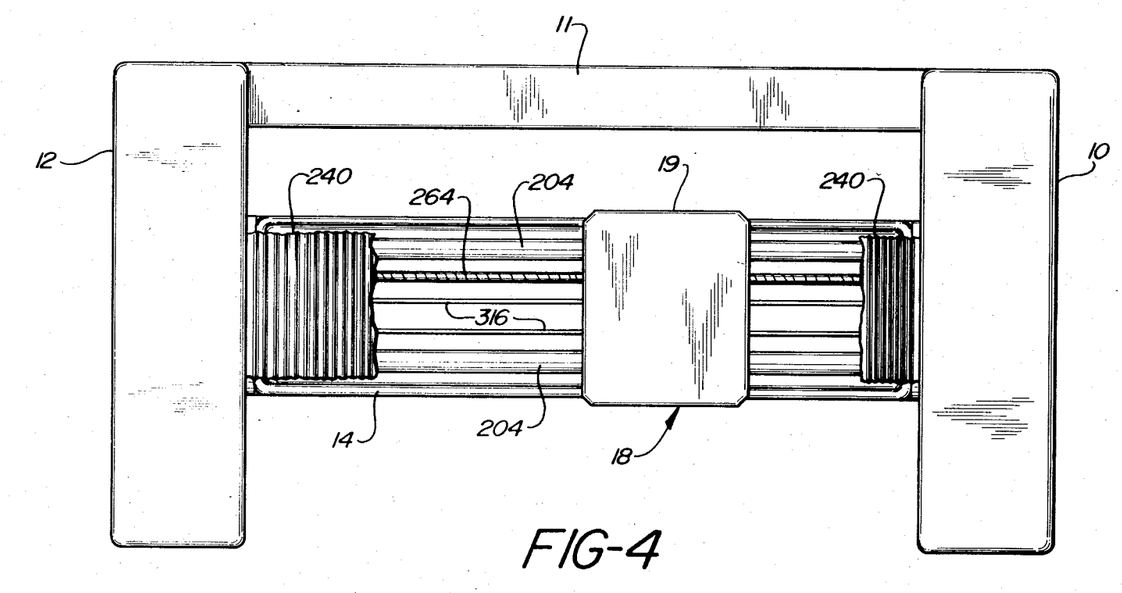
FIG. 4 is a top plan view of the positioner of FIG. 1.

Referring first to FIG. 1 there is shown in perspective an assembled medical diagnostic mechanical positioner including two spaced apart end supports such as a right end stand 10 and a left end stand 12 separated by about 7.5 feet, a distance sufficient to amply support most patients therebetween. Supported between the two end stands is a patient support such as area scan table 14 or, as shown in FIG. 2, ECT patient table 16. Either patient table is vertically adjustable by mechanism shown in FIG. 10, to be described in detail below.

Figure 13:
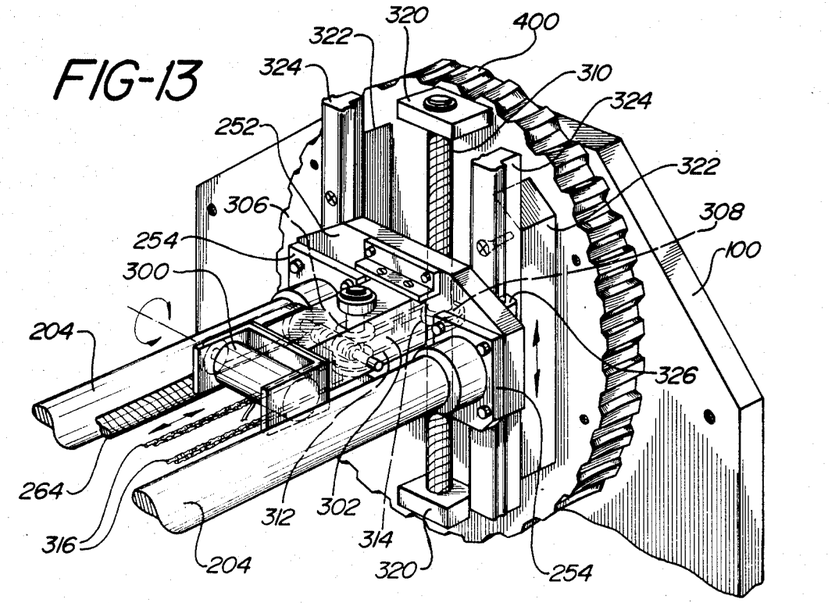
FIG. 13 is a perspective view showing vertical translation of the longitudinal support rods of FIG. 6.
Figure 14:
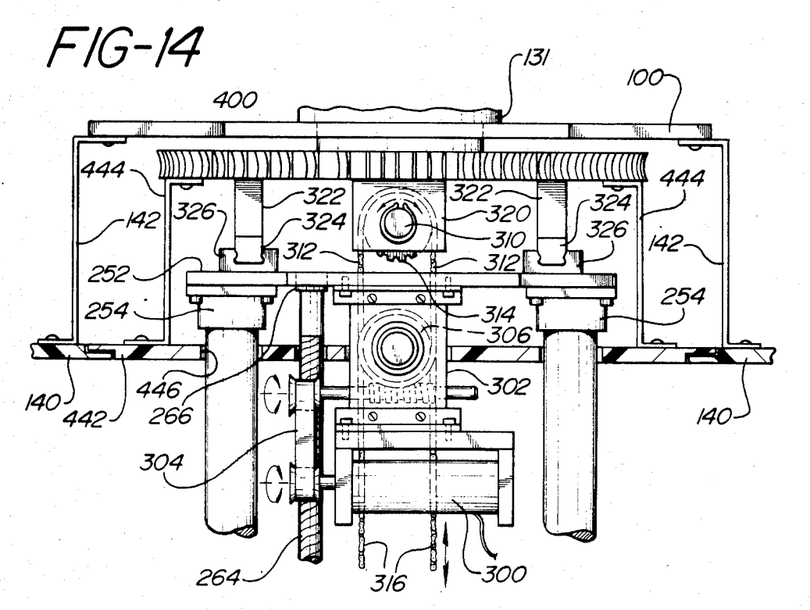
FIG. 14 is a top plan view of the structure shown in FIG. 13, partially in section.
Figure 15:
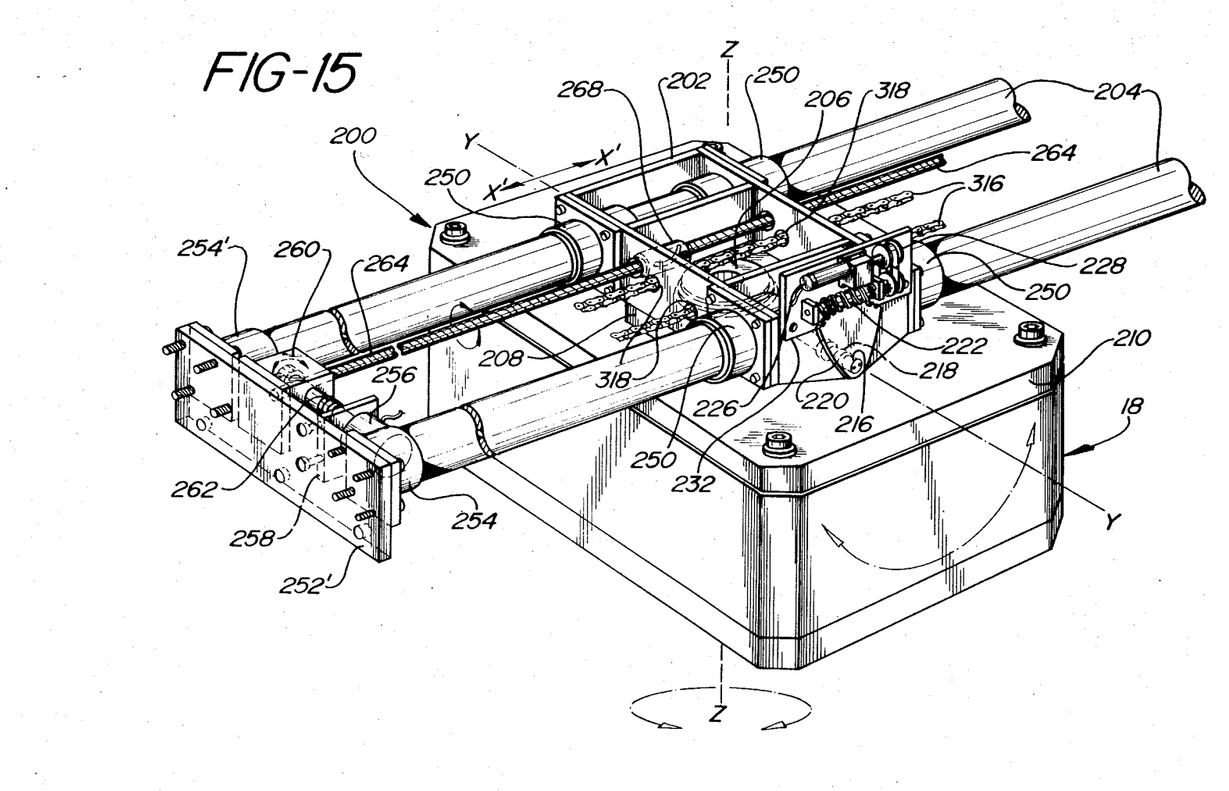
FIG. 15 is a perspective view of the camera head assembly of FIG. 1 with the top cover of the camera head assembly removed.
Figure 16:
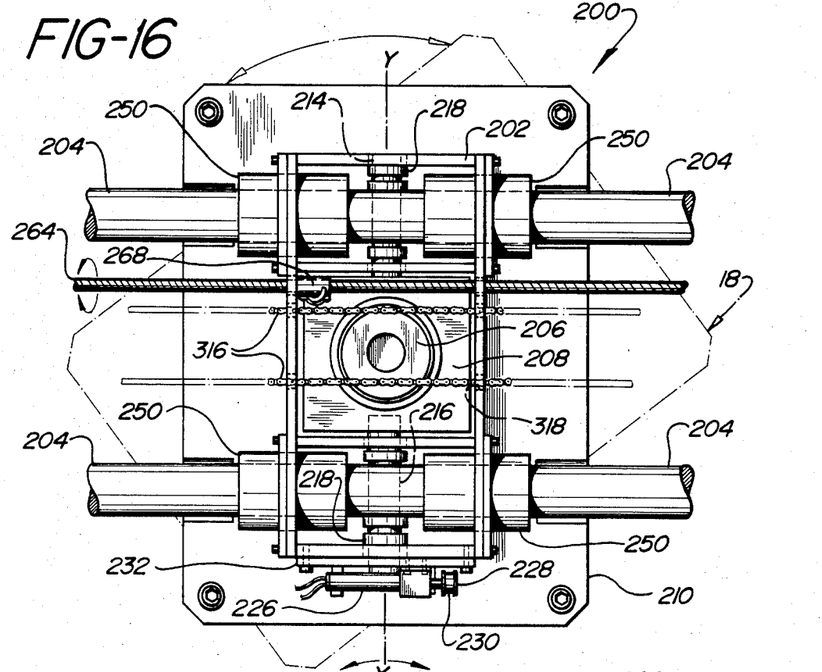
FIG. 16 is a top plan view of the camera head assembly of FIG. 15.
Figure 17:
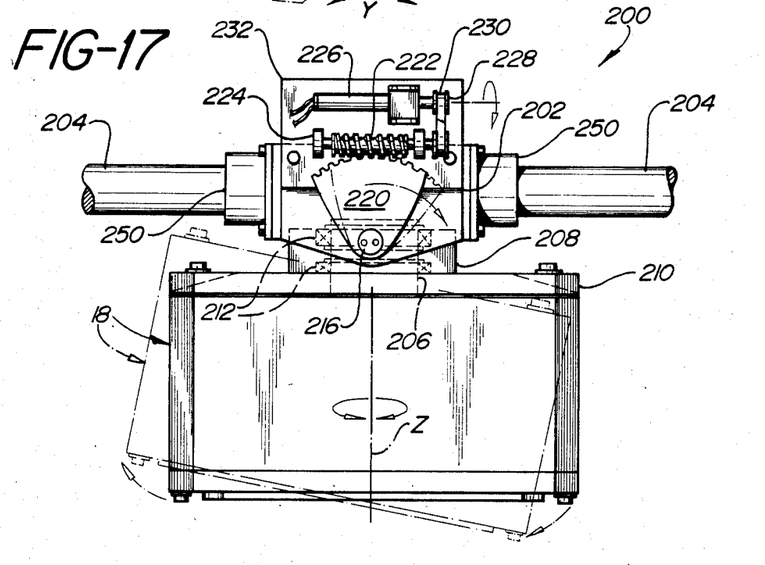
FIG. 17 is a front elevational view of FIG. 15.

Also provided between the two end stands is at least one piece of diagnostic machinery, typically a radiation detector, such as scintillation detector or gamma camera head 18, shown in detail in FIG. 15. Scintillation detector 18 is provided with six different and independent degrees of motion. The detector is laterally translatable by mechanism shown in FIG. 15 and described below. The detector is also pivotable about axis y—y as described below in connection with FIG. 16 as well as rotatable about axis z—z as shown in FIGS. 15 and 17. In addition, scintillation detector 18 is radially adjustable. This latter motion is accomplished within end stands 10 and 12 as illustrated in FIGS. 13 and 14 and as detailed in the discussion below. The detector is also tiltable relative to the plane defined by area scan table 14 and may be orbited about ECT patient table 16. Both of these motions are also accomplished within end stands 10 and 12 in a manner to be described below.

Figure 10:
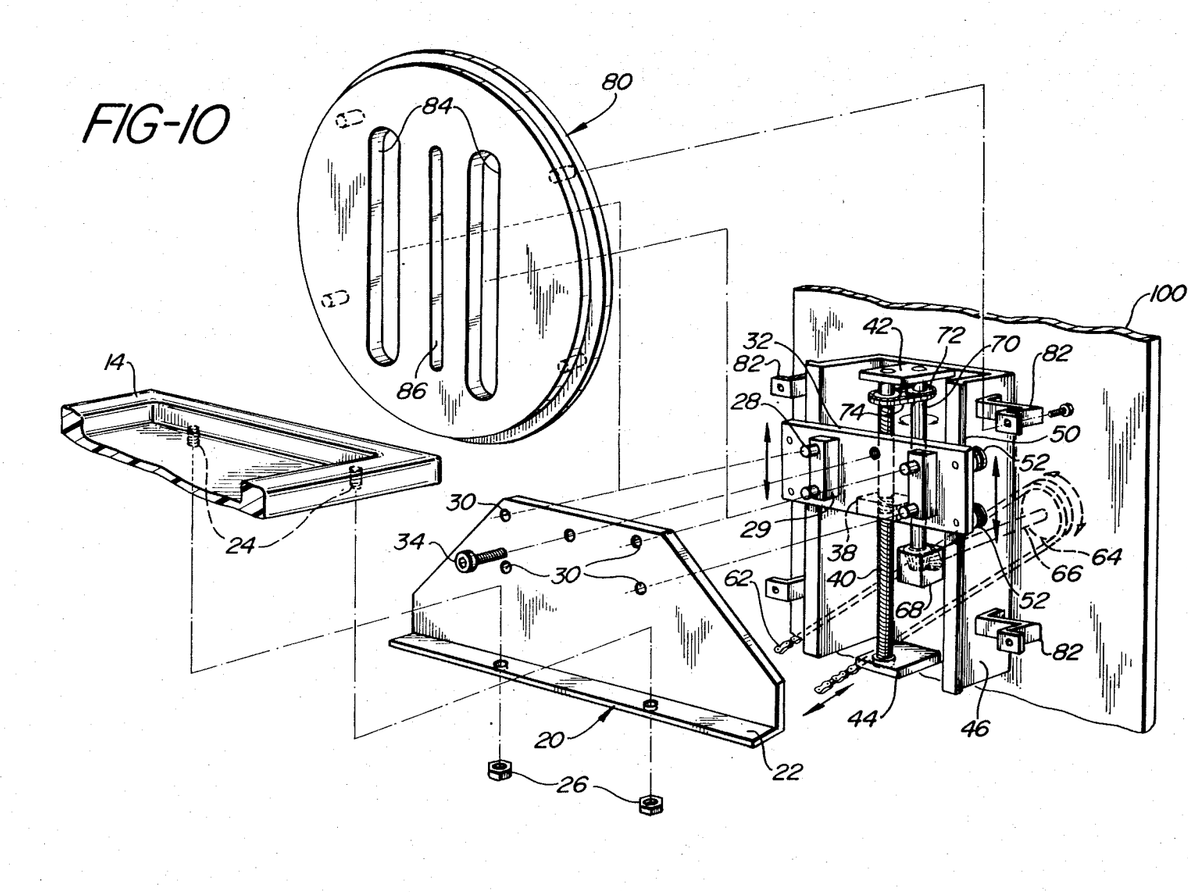
FIG. 10 is an exploded perspective showing vertical translation of the table positioner of FIG. 1.
Figure 11:
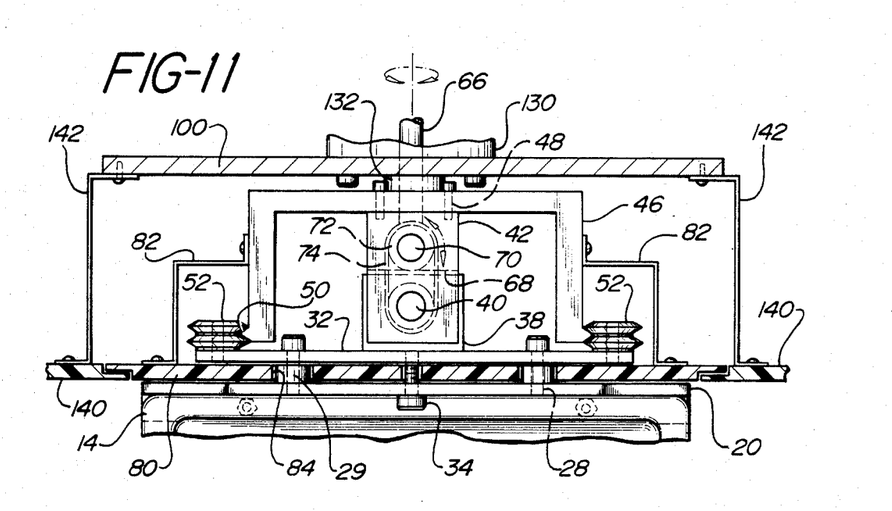
FIG. 11 is a top plan view of the assembled parts of FIG. 10, partially in section.

Means for vertical adjustment of the patient support will be discussed first with primary reference to FIG. 10. Either end of table 14 is supported by a bracket 20 (one shown) having a table support ledge 22 extending parallel to the generally horizontal orientation of area scan table 14. Table 14 is secured to the ledge 22 of bracket 20 by fastening means such as bolts 24 secured by nuts 26 in conventional fashion. Bracket 20 is aligned into position by means of four dowel pins 28 that protrude through matching apertures 30 provided therefor. The four dowel pins 28 protrude horizontally from a vertically adjustable plate 32. The bracket 20 is secured to the plate 32 by fastening means such as bolt 34. Attached to the rear of plate 32 is a housing that includes a non-rotating nut 38 through which a ball screw 40 is rotatable. Ball screw 40 is generally upright and is retained at its upper and lower extremity by flanges 42 and 44 each of which includes bearings to permit the ball screw 40 to rotate about its longitudinal axis. As the ball screw rotates, nut 38 rides up or down. Flanges 42 and 44 are secured to a U-shaped bracket 46 by convenient retaining means such as screws 48, shown in FIG. 11. U-shaped bracket 46 includes a pair of vertical wheel followers or V-shaped guides 50. In turn, end plate 32 is provided with right and left upper and lower wheels 52 configured and dimensioned to track guides 50 so as to maintain proper alignment of the patient table as it is raised and lowered.

Figure 7:
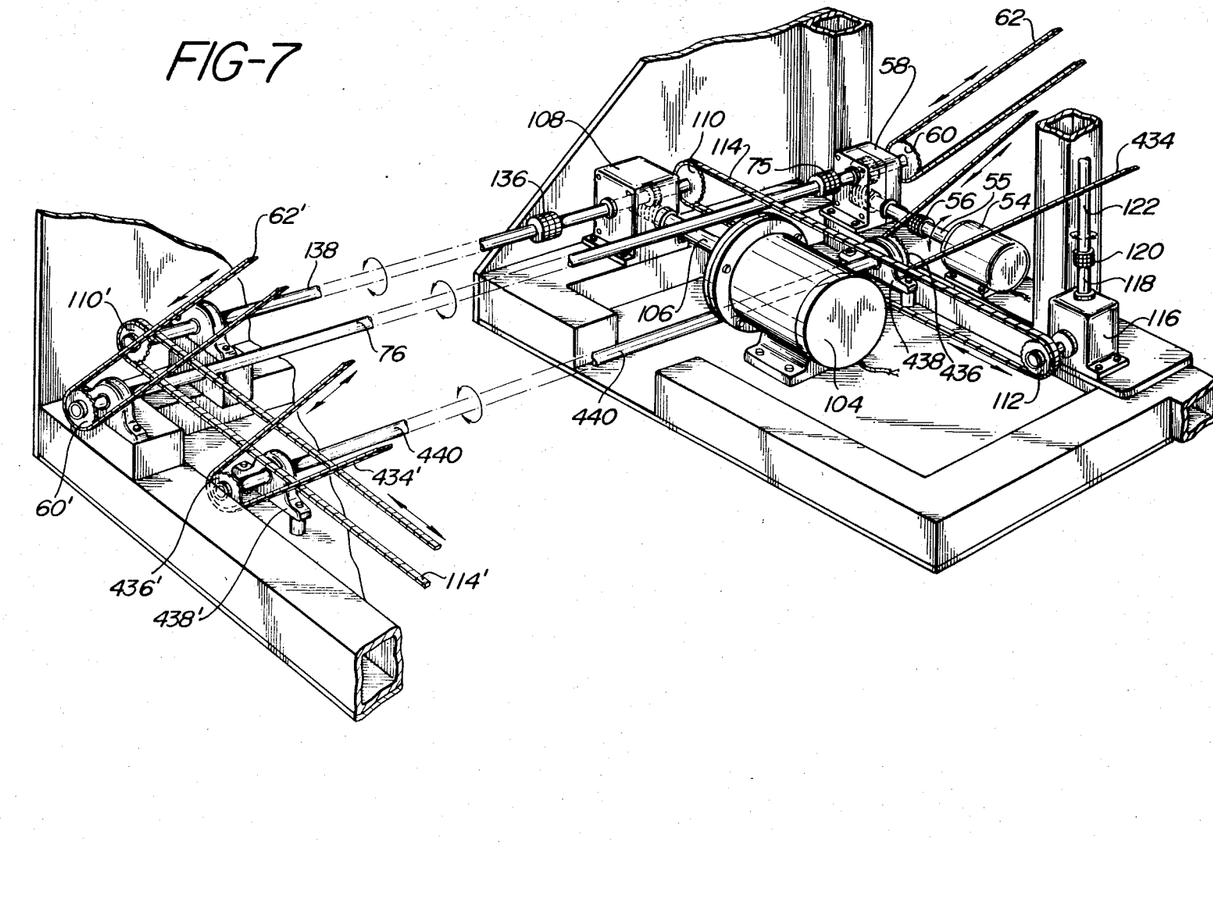
FIG. 7 is an enlarged perspective view showing a portion of the drive mechanisms illustrated in FIG. 6.

The power source for raising and lowering the patient table is preferably a single motor, shown in FIG. 7, such as a 0.25 horsepower permanent magnet DC motor 54, located in the base of end stand 10 and available from the Rae Corporation, McHenry, Ill. or the Reliance Company of Cleveland, Ohio. Output shaft 55 of the quarter horsepower DC motor 54 is connected by flexible coupling 56 into an 18:1 reduction ratio dual output worm gear box 58. One output of gear box 58 rotates a sprocket 60. About sprocket 60 is a chain 62 which is wound about a second sprocket 64, shown in dashed lines in FIG. 10, of the same ratio as the first sprocket 60 so that the two rotate at the same velocity. Connected to sprocket 64 is a lateral shaft 66 which, in turn, is connected to a 1:1 reduction ratio right angle gear box 68 disposed within U-shaped bracket 46. Also connected to the right angle gear box 68 is a vertical rotatable jackshaft 70 so that the rotation of shaft 66 rotates jackshaft 70. A sprocket 72 is provided at the top end of the jackshaft 70 and, by means of a chain 74, jackshaft 70 is coupled to ball screw 40 so that as shaft 70 rotates, ball screw 40 also rotates. Thus, power from motor 54 is transmitted to rotation of ball screw 40 which, in turn, raises or lowers nut 38 and, hence, one end of patient table 14.

Simultaneously, the second output of gear box 58 is connected to flexible coupling 25, thereby to conform the specification with the drawing which, in turn, rotates a one inch diameter 7.5 feet long shaft 76 which extends through stabilizer channel 11 to left end stand 12. The above described system is duplicated in left end stand 12. For ease of reference, a part located in left end stand 12 having a corresponding part in the right end stand 10 is designated by the same reference numeral as its counterpart followed by a prime. Thus, shaft 76 rotates sprocket 60' which engages chain 62' copying the action of chain 62. Since the dual outputs of worm gear box 58 are relatively low speed and high torque, power from motor 54 is harnessed to synchronously drive chains 62 and 62' so that both ends of table 14 are raised and lowered in unison thereby maintaining the table horizontal at all times including during height adjustment. Operator control of motor 54 for the height adjustment of table 14 is provided at control panel 78 or, alternatively, 78' disposed respectively at the front portion of end stands 10 and 12 for maximum convenience to the operator. As an alternative to motor 54, the vertical adjustment may be accomplished by other sources of power, such as by hydraulics or pneumatics or even manually. Moreover, the adjustment need not be accomplished by a single power source located at one end, but may include a pair of synchronized power sources, each controlling the height of one end of the patient table.

In general the function of any of the motors referred to in this application may be performed by an alternate power source. In addition, while the best mode contemplates a single power source for each of the four motions occurring within the end stands, a less desirable alternative would be a pair of power sources dedicated to each of these motions with the output of each such pair synchronized.

For cosmetics, a circular stationary cover plate 80 is provided at either end stand disposed between bracket 20 and end plate 32. A series of attachment brackets 82 are provided on U-shaped bracket 46 for affixing cover plate 80 in place. Cover plate 80 is provided with a pair of vertical slots 84 and a centrally located third slot 86 to permit the patient table to be raised and lowered. Slots 84 are configured and dimensioned to permit vertical passage therein of spacers 29. Slot 86 is similarly provided to allow for bolt 34. The two spacers 29 are designed somewhat thicker than the thickness of cover plate 80 to avoid friction by providing some separation on either side of cover plate 80 and the two moving parts, bracket 20 and end plate 32.

Figure 6:
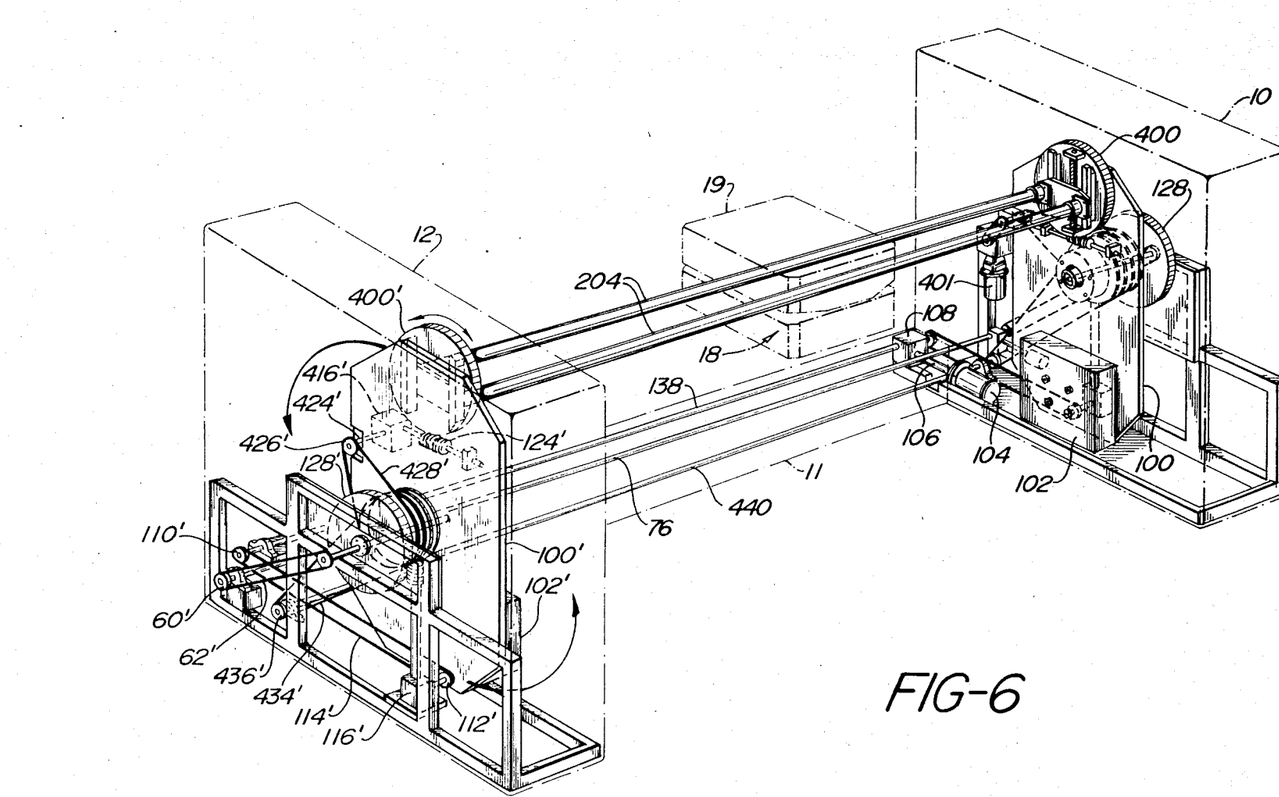
FIG. 6 is a schematic perspective view of selected portions of the positioner of FIG. 1 with the end stand covers removed and the bellows removed from about the scintillation detector support rods.

In accordance with the above-described apparatus, the height of either the area scan table or the ECT patient table is adjustable for added convenience of patient transfer. In addition it may also be desirable to displace somewhat scintillation detector 18 and its support structure as a patient is positioned on one of the tables. To do so, the scintillation detector and support structure is rotatable independent of the vertical position of the patient table by rotation of system rotate means including two rotatable members such as system rotate main plates 100 and 100', one located at each end stand, as shown in FIG. 6.

The two system rotate main plates are substantial metal plates which are sufficiently strong to support scintillation detector 18 and its support structure as well as a pair of counterweights 102, 102' (one on each system rotate plate) or, alternatively, two detector heads and their associated support structures such as in a dual headed ECT system, as illustrated in FIG. 2. Power for rotation of the system rotate main plates is provided preferably single by a 0.75 horsepower permanent magnet DC motor 104 such as a 2375 rpm 90 volt motor available from the Rae Corporation, McHenry, Ill. 60050.

Figure 8:
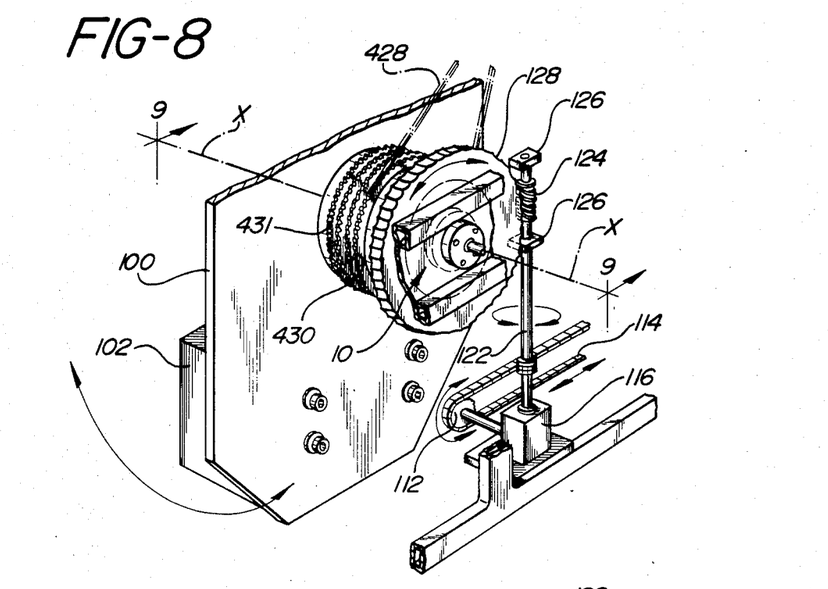
FIG. 8 is a perspective view partially broken away showing portions of the right side system rotate subassembly of FIG. 6.
Figure 9:
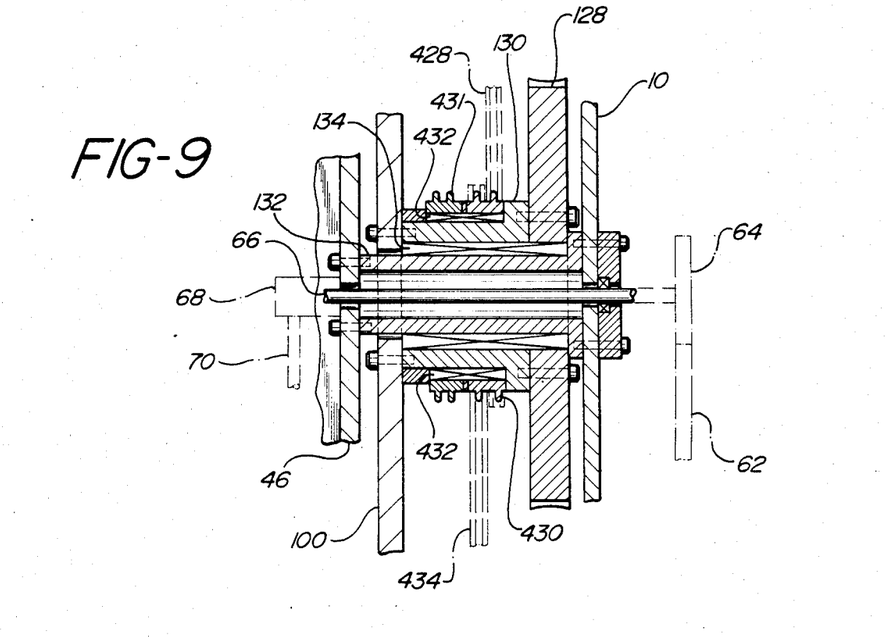
FIG. 9 is a cross-sectional view taken along line 9—9 of FIG. 8.

As illustrated in FIG. 7, the motor 104 is positioned in the base of right end stand 10 though its power is applied to both system rotate plates 100, 100' to drive them synchronously in a fashion similar to the manner in which 0.25 horsepower motor 54 is used. Motor 104 rotates a shaft 106 which is coupled to a gear reducer such as a 10:1 reduction ratio double output worm gear box 108. The two outputs of gear reducer 108 rotate at a lower speed than shaft 106 and have higher output torque. One output of the gear box 108 is connected to a sprocket 110 which is coupled to a corresponding sprocket 112 by means of chain 114. In turn, sprocket 112 drives a 1:1 ratio right angle gear box 116 which couples the high torque low speed of sprocket 112 to rotation of vertical jackshaft 118. Jackshaft 118 is coupled to a coaxial shaft 122 by means of chain coupling 120. Shaft 122, as seen in FIG. 8, rotates worm 124 retained in position for rotation by a pair of bearings such as Timkin tapered bearings 126. Worm 124 meshes with a worm gear 128 preferably having an 18 inch pitch diameter yielding a 108:1 reduction ratio. Worm gear 128 is attached to system rotate plate 100 by means of rim 130 (FIG. 9). Rim 130 is secured annularly on one side to worm gear 128 and on its other side to system rotate plate 100. Thus, worm gear 128 and system rotate plate 100 are affixed to each other and rotate about spindle 132 by roller bearings 134 such as are available from a company called TRW. Spindle 132 is fixedly secured at one end thereof to end stand 10 thereby defining common rotational axis x—x about which system rotate main plates 100 and 100' rotate.

End plate 100' is driven synchronously with end plate 100 as follows. Second output of gear reducer 108 is attached by means of flexible chain coupling 136 to a one inch diameter, 7.5 foot long shaft 138 that is positioned within stabilizer channel 11 and which rotates sprocket 110' disposed within left end stand 12. Sprocket 110' connects to a corresponding sprocket 112' by means of chain 114', as shown in FIG. 7, and, hence, the mechanism for rotating system rotate plate 100' is duplicated identically within left end stand 12. The combination of the 10:1 reduction ratio of gear reducer 108 and the 108:1 gear reduction between worm 124 and worm gear 128 (as well as between corresponding worm 124' and its associated worm gear 128') allows power of relatively low torque to be simultaneously applied to both worms 124, 124' from the single motor 104 located in only one end stand 10 without excessive end-to-end windup expected from deflections of the components that couple power to the non-motorized end stand 12. Thus, both system rotate plates 100, 100' are driven synchronously from the single motor 104.

Figure 12:
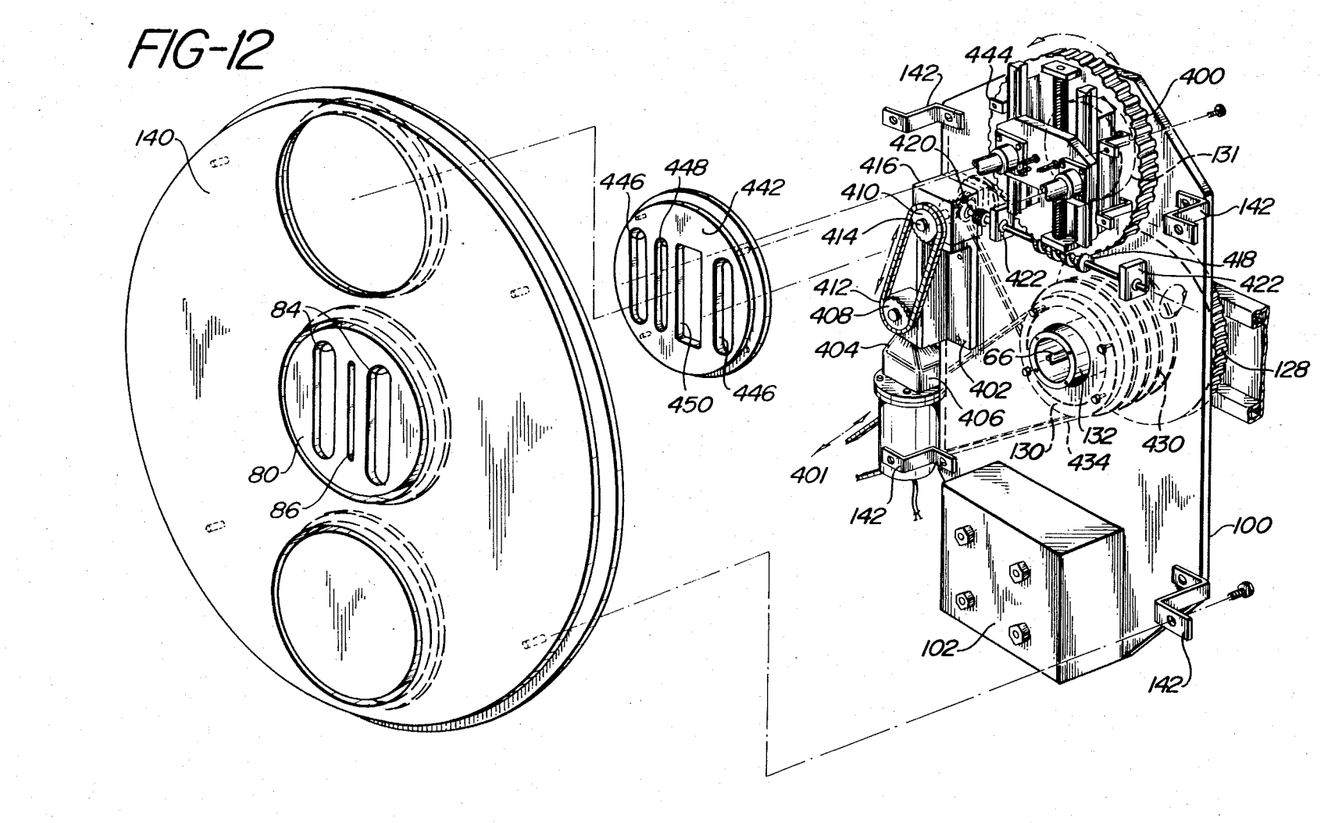
FIG. 12 is a perspective view showing small wheel rotation of FIG. 6.

Concealing system rotate plate 100 is circular access panel 140 which is secured to the system rotate plate by a plurality of brackets 142, as illustrated in FIG. 12. Centrally disposed within access panel 140 is the cover plate 80 which remains stationary during rotation of access panel 140. Though not shown, a second access plate is provided at left end stand 12 to cover system rotate plate 100' and the hardware supported thereon.

Rotation of system rotate means thus permits scintillation detector 18 to be rotated, for example, back toward the 9 o'clock position to make it more convenient for a patient to be transferred onto area scan table 14. In addition, emission computed tomography can be routinely accomplished by orbiting the scintillation detector 18 about longitudinal axis x—x passing through the long axis of the patient by synchronous rotation of system rotate plates 100 and 100'.

As shown in FIG. 15, scintillation detector 18 is retained by a detector support means such as assembly 200 that includes a carriage such as movable fitted collar 202 and longitudinal positioners such as a pair of 2.5 inch diameter solid steel positioning rods 204. Removable cover 19, shown in FIG. 1, normally conceals carriage 202. Scintillation detector 18 is attached to carriage 202 by a 4.5 inch diameter shaft 206 that is secured to an intermediate support block 208 and to top plate 210. The large diameter shaft 206 is rotatable about axis z—z by means of two large tapered roller bearings 212 (FIG. 17) such as available from the Timken Roller Bearing Company. The roller bearings 212 are separated by about two inches as diagrammatically illustrated in FIG. 17. The combination of shaft 206 and roller bearings 212, renders camera head 18 manually rotatable about axis z—z as might be required to alter the field of view orientation of the scintillation detector. Top plate 210 is secured to shaft 206, and, hence rotates relative to the carriage assembly 202 as scintillation detector 18 is rotated, as depicted in FIG. 16. If desired, this motion may also be power assisted.

Support block 208, in turn, is connected pivotally to carriage 202 by means of a pair of laterally oriented 1.25 inch diameter support shafts 214 and 216. The two support shafts 214, 216 are each housed in linear bearings 218 which permit limited pivotal motion about axis y—y between the detector head and the carriage 202. To accomplish this pivotal motion remotely, support shaft 216 extends through fitted carriage 202 and is connected to a worm gear 220 (FIG. 17) whose gears mesh with worm 222 such that rotation of worm 222 results in rotation of gear 220 about pivotal axis defined by shaft 216. Worm 222 is mounted for rotation by means of a pair of bearings 224. The worm 222 is powered by a conventional gear motor 226 whose output is coupled to the worm by a 1:1 ratio timing pulley pair 228 connected by a timing belt 230. The motor 226 is mounted on a motor mounting plate 232 which is secured to the carriage 202.

The effect of pivoting detector 18 about axis y—y relative to a stationary patient lying horizontally can be duplicated alternatively by maintaining the detector level and adjusting the table to a non-horizontal orientation, in effect, pivoting the table about an axis parallel to axis y—y. This may be accomplished by adjusting the two ends of the table to different heights or adjusting the two ends of the positioning rods 204 to different heights.

In addition to rotating the camera head about axis z—z to alter its field of view and pivoting the camera about axis y—y to alter the detection plane, the radiation detector or other supported diagnostic equipment is laterally translatable by lateral displacement means in a direction defined by the longitudinal orientation of positioning rods 204. Carriage 202 is attached to each of positioning rods 204 by means of five inch long linear ball bearings 250 such as made by the IKO Company of Japan. As shown in FIG. 13, one end of both positioning rods 204 is supported by fitted retaining members 254 which, in turn, are bolted to support plate 252, all contained within right end stand 10. The other ends of the two positioning rods 204 are supported by support plate 252' by means of fitted retaining members 254' located within left end stand 12. As shown in FIGS. 1 and 2, bellows 240 are provided to normally conceal positioning rods 204.

For power assisted lateral displacement of the scintillation detector 18 between the two support plates 252 and 252' there is provided mechanism preferably powered by a 0.125 horsepower DC permanent magnet motor such as motor 256 diagramatically depicted in FIG. 15 and obtainable from the Rae Corporation of Illinois. Motor 256 is retained in position by means of a lateral plate 258 which is bolted to support plate 252'. The output of motor 256 is attached to a 10:1 reduction ratio worm gear box 260 by flexible coupling 262. The output of the worm gear box, in turn, is rigidly coupled to a 7.5 foot long steel ball screw 264 which spans the two end stands and extends through the fitted carriage 202. The ball screw 264 is supported at its other end on a bearing 266, shown in FIG. 14, attached to support plate 252. A portion of ball screw 264 rotates within nut 268 which is attached to fitted carriage 202 so that as ball screw 264 rotates about its longitudinal axis in response to the output of worm gear box 260, fitted carriage 202 together with scintillation detector 18 is translated between the two end stands 10 and 12. Such translation is required for two dimensional whole body imaging accomplished by maintaining system rotate plates 100 and 100' stationary while moving the scintillation detector 18 in a direction parallel to the longitudinal axis of the patient.

To provide adjustment in the vertical direction or, more generally, to alter the radial separation between the patient table and the scintillation detector, the entire detector support assembly 200 is radially displacable relative to the centers of system rotate plates 100 and 100'. Radial displacement is accomplished by the synchronous displacement of end plates 252 and 252' powered preferably by a single 0.25 horsepower permanent magnet DC motor such as motor 300 shown in FIG. 13 and available from the Rae Corporation. The output of the 0.25 horsepower motor 300 is linked to an 20:1 reduction ratio worm gear box 302 by means of a timing belt 304, shown in FIG. 14. The output of gear box 302 drives a sprocket 306 which is coupled by chain 312 to a nut 308 (FIG. 13) that rides on ball screw 310. Nut 308 is bearing mounted and, hence, is permitted to rotate about ball screw 310 in conventional fashion. Nut 308 is also connected to a second sprocket 314 which drives a 7.5 foot long chain 316.

As shown in FIG. 15, the 7.5 foot long chain 316 passes through apertures 318, two per side, of fitted carriage 202 and is attached to a sprocket 314'. Correspondingly, sprocket 314' is attached to a nut 308' on ball screw 310' located behind support plate 252' such that the mechanism for raising and lowering positioning rods 204, exclusive of the power source, is duplicated. Thus, as motor 300 is empowered, chain 316 is driven and simultaneously rotates nuts 308 and 308' about stationary ball screws 310 and 310', respectively. Ball screw 310 is supported at either end by small plates 320 which, in turn, are secured to an 18-inch pitch diameter head rotation worm gear 400. Also attached to worm gear 400 are a pair of elongated spacer bars 322 each of which supports an IKO made linear way 324. Each linear way 324 engages a linear bearing 326 secured to support plate 252 on the side opposite fitted retaining members 254. The identical hardware is duplicated on corresponding worm gear 400' disposed in left end stand 12. Thus, as nuts 308 and 308' are rotated, positioning rods 204 are raised and lowered relative to ball screw 310 orthogonal to the direction defined by rods 204 and horizontal axis x—x. The combination of the synchronous rotation of system rotate main plates 100 and 100' and the radial displacement adjustment just described permits the positioner to perform ECT studies at a range of operator selectable radii.

In accordance with the best mode, the multipurpose mechanical diagnostic imaging support structure is also capable of longitudinally slanting detector 18 relative to the patient support such as by rotating each pair of support rods 204 about a longitudinal axis parallel to and half way between the longitudinal axes of the rods. This is accomplished preferably by a single power source and is arranged for operation regardless of the orientation of system rotate plates 100 and 100' and is performed either while the system rotate plates are stationary or in motion. Typically, this motion is undertaken to direct the orientation of a scintillation detector relative to a portion of a patient, for example, to better focus on a selected region of the patient's anatomy.

Figure 5:
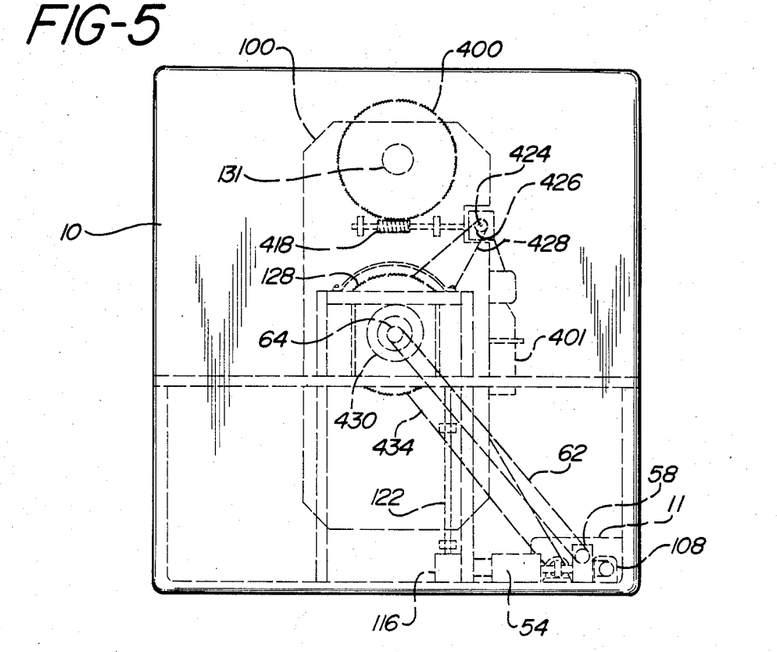
FIG. 5 is a right side elevational view of the positioner of FIG. 1.

The power source for this minor rotation is preferably a 0.5 horsepower DC permanent magnet motor such as motor 401 available from the Rae Corporation. As shown in FIG. 12, the output of motor 401 is coupled to a single output 10:1 reduction ratio worm gear box 404 by use of a C flange cup 406. Gear box 404 is secured to system rotate main plate 100 by fastening means such as bracket 402 and is connected to rotate a sprocket 408 which is coupled to a like sized sprocket 410 by a chain 412. Sprocket 410 drives shaft 414 of a dual input shaft 1:1 reduction ratio right angle gear box 416 which is also mounted on system rotate main plate 100 by means of bracket 402. The right angle gear box 416 output is coupled to a worm 418 by chain coupling 420. Worm 418 meshes with the 18-inch pitch diameter head rotation worm gear 400 resulting in a 108:1 reduction ratio. Worm gear 400 is rotatably attached to system rotate main plate 100 by bearing 131, depicted in FIG. 14. Either end of worm 418 is journaled into bearing mounts 422 which are secured to system rotate main plate 100 to thereby maintain worm 418 engaged to worm gear 400. As shown in dashed lines in FIG. 5, the second input 424 of the right angle gear box 416 protrudes through system rotate main plate 100 and connects to a sprocket 426 on the other side of the plate. Sprocket 426 is coupled by means of chain 428 to a large, floating dual sprocket 430, illustrated in FIGS. 8 and 9, and disposed about the central rim 130. Sprocket 430 is positioned for rotation about rim 130 by means of bearings 432 so that sprocket 430 is rotated by chain 428 regardless of the position of gear box 416. Sprocket 430 is about three times the size of sprocket 426 resulting in an approximate 3:1 reduction ratio.

Dual sprocket 430 also engages a second chain 434 which, as shown in FIG. 7, is attached to a sprocket 436 comparable in size to sprocket 426 and hence resulting in a 1:3 ratio. Sprocket 436 is supported by a pillow block 438 and is attached to a one-inch diameter 7.5 foot long shaft 440 which extends through stabilizer channel 11 to end stand 12. Within end stand 12, shaft 440 is supported by a pillow block 438' having a sprocket 436' at its end. Attached to sprocket 436' is chain 434' connected to drive another dual sprocket 430' which duplicates the motion of sprocket 430. The remaining portion of the mechanism except for the power source is duplicated within left end stand 12. This provides for synchronous and identical rotation of worm gears 400 and 400' driven by the single motor 401. According to this configuration, the power from motor 401 is not only coupled to rotate worm gear 400, but through the use of the two dual sprockets, to synchronously rotate worm gear 400', even during rotation of system rotate main plates 100 and 100'.

Since rotation of worm gear 400 may be desired regardless of the angular orientation of system rotate main plate 100 to permit such synchronous slanting, care must be exercised to be sure the attitude of the detector relative to a fixed axis is maintained during rotation of the system rotate main plates. This is passively accomplished in the foregoing mode, as will be appreciated from FIG. 5, since rotation of main plate 100 forces rotation of chain 428 about sprocket 426 of gear box 416. Rotation of chain 428 also rotates dual sprocket 430 which then rotates chain 434 so that by means of rotation of shaft 440, the motion is duplication in the left end stand. The rotation of shaft 440, sprocket 430, and sprocket 430' is such as to exactly compensate for the fact that worm gear 400 is free to rotate relative to main plate 100. Thus, the maintenance of the attitude of the detector relative to the axis of rotation of the main plates is assured.

Again, for cosmetics, a cover plate 442 (FIG. 12) is provided in the plane defined by access panel 140 to cover worm gear 400 and its associated hardware. Cover plate 442 is secured by a series of brackets 444 directly to worm gear 400 so that it rotates with worm gear 400 as well as with system rotate main plate 100. Elongated slots 446 are provided in cover plate 442 to permit movement of positioning rods 204. A separate off-center elongated slot 448 is provided for passage of ball screw 264 and, finally, rectangular opening 450 is provided to accommodate ball nut 308 and the chains from gear box 302, as illustrated in FIG. 14.

In an alternate embodiment, counterbalance 102, 102' are replaced by second worm gears 400, 400' on system rotate main plates 100, 100' in order to support a second detector such as a gamma camera and a second detector support assembly 200. If so, then the mechanism described above is duplicated by use of a second floating dual sprocket 431 disposed adjacent sprocket 430. The assembled arrangement is depicted in the perspective diagrammatical illustration of FIG. 2.

As a further variation, there may be provided two scintillation detectors 18 supported on a single detector support assembly 200. Such an arrangement would permit imaging a larger area of interest without requiring lateral translation of a single detector.

Each of the above-described motions are independent of the others and may be performed separately or in any desired combination. Thus, for example, the orbital motion of the scintillation detector about the patient table during an ECT study may be accomplished in circular fashion without adjusting the radial separation between the patient table and the detector. Alternatively, the radial separation may be synchronized with the orbital rotation such that the actual path defined by the scintillation detector becomes non-circular, as may be desired to obtain enhanced tomographic image quality. Further, the detector may be rotated or pivoted to alter detector focus from a central radius.

We claim:

1. A diagnostic imaging system empolying a scintillation camera detector, comprising:
   (a) two spaced apart end supports;
   (b) a patient table spanning and attached to said end suoports;
   (c) detector support means spanning and attached to said end supports in predetermined association with said patient table; and
   (d) means, contorllably slidably mounted on said support means, for carrying said scintillation camera detector; and
   (e) means for independently varying each of (i) the displacement of said means for carrying along said support means. (ii) angular displacement of said camera relative to said means for carrying, and (iii) rotational displacement of said camera relative to said means for carrying.

2. The apparatus according to claim 1 further comprising vertical adjustment means for further independently varying said patient table at a generally horizontal orientation within a selectable range of heights relative to the par of end supports.

3. The apparatus according to claim 2 wherein said vertical adjustment means for adjusting the height of said patient table comprises means for raising and lowering said patient table at either end thereof synchronously.

4. The apparatus according to claim 1 futher comprising system rotate means for further independently rotating said detector support means in both end supports simultaneously so that said radiation detector is orbited about said patient table.

5. The apparatus according to claim 4 wherein said system rotate means comprises a rotatable member disposed in each end support for rotation about a fixed and common axis and a single power source whose power is coupled to simultaneously rotate both of said rotatable members.

6. The apparatus according to claim 5 further comprising radial displacement means for altering the radial displacement of said detector support means relative to the common axis about which said rotatable members rotate.

7. The apparatus according to claim 6 wherein said radial displacement means comprises a single power source whose power is coupled to both end supports simultaneously so that said detector support means is adjusted at either end synchronously.

8. The apparatus according to claim 5 further comprising means for slanting said detector support means within both end supports thereby altering the orientation of said radiation detector relative to said patient table.

9. The apparatus according to claim 8 wherein said slanting means includes a single motor mounted on one of said rotatable members and further comprising means for synchronously applying power from said single motor to simultaneously slant said detector support means at either end thereof.

10. The apparatus according to claim 9 wherein said single motor is mounted on one of said rotatable members such that when said rotatable members are being rotated and no power is applied to said slanting means the detector maintains a fixed attitude, relative to said common axis.

11. The apparatus according to claim 1 and further comprising: a second scintiallation camera; second detector support means spanning and attached to said end supports, spaced apart from said patient support generally opposite said first detector support means, said second support means having mounted thereon means for carrying said second scintillation camera and means for independently varying each of (i) the displacement of said second means for carrying along said second support means, (ii) angular displacement of said second camera relative to said second means for carrying, and (iii) rotational displacement of said second camera relative to said second means for carrying.

12. The apparatus according to claim 1 further comprising a second detector supported by said detector support means.

13. A medical diagnostic system comprising:
(a) two spaced apart end supports;
(b) a patient table supported at either end thereof by said end supports;
(c) a radiation detector;
(d) detector support means attached at either end to one of said end supports for supporting said radiation detector at a location intermediate said two end stands and spaced apart from said patient support;
(e) wherein said means for supporting said radiation detector comprises a carriage to which said detector is mounted, a pair of parallel rods spanning the space between said pair of spaced apart end supports for together retaining said carriage, and means for laterally displacing said carriage along the length of said rods between said two end supports; and
(f) apparatus further comprising means for pivoting the radiation detector relative to said carriage about an axis intersecting said carriage and orthogonal to the longitudinal axes of said rods.

14. A medical diagnostic system comprising:
(a) two spaced apart end supports;
(b) a patient table supported at either end thereof by said end supports;
(c) a radiation detector;
(d) detector support means attached at either end to one of said end supports for supporting said radiation detector at a location intermediate said two end stands and spaced apart apart from said patient support;
(e) wherein said means for supporting said radiation detector comprises a carriage to which said detector is mounted, a pair of parallel rods spanning the space between said pair of spaced apart end supports for together retaining said carriage, and means for laterally displacing said carriage along the length of said rods between said two end supports; and
(f) means for altering the orientation of the radiation detector relative to said carriage with reference to a first axis orthogonal to the longitudinal axes of said rods and intersecting said patient table.

15. The apparatus according to claim 14 further comprising means for pivoting the radiation detector relative to said carriage along an axis orthogonal to the longitudinal axes of said rods and to said first axis.

* * * * *